US006933478B2

(12) United States Patent
Lewis

(10) Patent No.: US 6,933,478 B2
(45) Date of Patent: Aug. 23, 2005

(54) JOINT HEAT

(76) Inventor: Daniel Houston Lewis, 4615 Empire Ave., Jacksonville, FL (US) 32207

( * ) Notice: Subject to any disclaimer, the term of this patent is extended or adjusted under 35 U.S.C. 154(b) by 0 days.

(21) Appl. No.: 10/657,035

(22) Filed: Jul. 1, 2005

(65) Prior Publication Data

US 2005/0051537 A1 Mar. 10, 2005

(51) Int. Cl.[7] ................................. H05B 3/44
(52) U.S. Cl. ...................... 219/544; 219/211; 219/549; 607/108
(58) Field of Search ................. 219/211, 544, 219/549; 2/102; 607/110, 112, 108, 96, 98, 99, 109, 111

(56) References Cited

U.S. PATENT DOCUMENTS

| | | | |
|---|---|---|---|
| 551,939 A | 12/1895 | Weber | 128/403 |
| 723,797 A | 2/1903 | Williams | 128/379 |
| 1,594,053 A | 7/1926 | Evans | 128/379 |
| 2,071,706 A | 2/1937 | Reach | 128/380 |
| 2,429,583 A | 10/1947 | Ogle | 128/380 |
| 3,178,559 A | 4/1965 | Fogel et al. | 219/528 |
| 3,680,563 A | * 8/1972 | Forrest | 607/112 |
| 3,889,684 A | 6/1975 | Lebold | 128/403 |
| 4,042,803 A | * 8/1977 | Bickford | 219/211 |
| 4,061,897 A | * 12/1977 | Thykeson | 219/211 |
| 4,303,074 A | * 12/1981 | Bender | 607/96 |
| 4,512,830 A | 4/1985 | Hulett et al. | 128/380 |
| 4,676,246 A | * 6/1987 | Korenaga | 607/153 |
| 4,891,501 A | * 1/1990 | Lipton | 607/110 |
| 5,032,705 A | * 7/1991 | Batcheller et al. | 219/211 |
| 5,480,418 A | * 1/1996 | Zeoli-Jones | 607/110 |
| 6,185,744 B1 | * 2/2001 | Poholski | 2/102 |

FOREIGN PATENT DOCUMENTS

AT        191084        9/1956 .................. 128/3

* cited by examiner

Primary Examiner—Robin O. Evans
Assistant Examiner—Leonid Fastovsky

(57) ABSTRACT

An electric heating device that is constructed in a unique fashion that allows it to be drapeable so that its three-dimensional, 'scoop-like' shape fits the curvature of a relaxed shoulder, a crooked knee or a crooked elbow, and is held in place by an adjustable strap whose ends are attached to the device. The heating element configuration that is contained within a singular, sealed, water-tight vinyl envelope that is produced as one piece, with the three panels briefly connected at a point where the heating element wiring crosses from one panel to the other.

3 Claims, 3 Drawing Sheets

JOINT HEAT

BACKGROUND OF THE INVENTION

The present invention relates to an electric heating device, and more particularly to an electric heating device for providing bilateral heat for treatment of related muscle groups, tendons and nerve bundles associated with three body joints: the shoulder, elbow and knee.

It is a well-known fact that heat is helpful in the therapeutic treatment of injured skeletal muscles and connective tissues. The application of increased heat causes the dilation of the blood vessels (vasodilatation) which increases blood flow to treated areas, thereby, speeding up the healing process.

It is also known that muscle injuries often occur sequentially in muscle groups and their tendons. For example, muscles associated with the movement of the shoulder are the Deltoideus, the Terus Major and Minor, the Pectorallis Major and the Latissimus Dorsi. Muscles associated with the movement of the elbow are the Pronator Terus and the Flexor Carpi Radialis. Muscles associated with the movement of the knee are the Vastus Medialis, the Vastus Lateralis and the Rectus Femoris.

In order to receive maximum, satisfactory therapy to these three body joints, it is necessary to apply constant, even, blanket heat coverage to these and all other muscles and tendons associated with the affected joint.

However, even though there are numerous brand choices on retailers' shelves, all of them are of the flat, rectangular variety, which are acceptable for flat areas of the body, but suffer from certain disadvantages in convenience of use when applied to curved body joints, specifically the shoulders, the elbows and knees.

It is not possible to accomplish full coverage of these areas without uncomfortable binding or "cuffing" of the flat pad against those areas being treated.

In order to affix or secure a flat heating pad to these three body joints, one must be creative. Some users use duct tape or large towels to hold the pads in place.

Furthermore, the resulting pockets of air decrease the efficiency of heat transfer from the pad to the object over which it is draped. Creasing and bending of the heating elements causes a separation of the heating element from the enclosure and increases the bulkiness of the heating pad, rendering the pads 'undrapeable'.

In summary, it is difficult to achieve satisfactory heat therapy to the shoulder, elbow or knee joints with the use of a flat heating pad.

BRIEF SUMMARY OF THE INVENTION

The subject of this invention presents several advantages over the prior art.

The flat electric heating pad is not designed to blanket the entire shoulder, elbow or knee, and, therefore, will not provide the needed heat to all of the muscle groups associated with these joints, and will allow most of the heat to escape from around the unsecured edges of the pad.

Many users resort to bending their flat, rectangular pad, in an attempt to reshape it to fit one of these body joints.

As a result of this "square peg/round hole" configuration, some people experience 'hot spots' from the unevenness caused by this misuse.

On the other hand, the pocket formed by the unique, three-dimensional, curved structure of the instant device provides a comfortable envelope that completely enwraps and silhouettes the entire area of these three targeted joints, capturing most of the heat.

In addition, simply from a practical standpoint, it is a difficult task for users to hold a flat electric heating pad to their shoulders, elbows or knees for any length of time, and are forced to take extraordinary measures, such as the use of duct tape.

However, the adjustable strap of the instant device holds the heating device securely and comfortably in place, while allowing constant, even heat therapy to the entire affected area.

DETAILED DESCRIPTION OF THE INVENTION

The instant electric heating device is actually three heating pads with one electric source and one controller, sewn together, with their enclosed heating elements connected at a narrow, one inch outer edge of the connected pads.

The isolation of this connection to the outer edge allows for the free flexure of the pads at the their connected seams.

One of the three pads is rectangular in shape—approximately 3½ inches to 4½ inches in width and approximately 14 inches to 16 inches in length. This becomes the center panel of the device, to which two triangular side panels are attached.

The two triangular side panels are duplicates of each other, and will become the sides or walls of the device. They are cut in the basic form of a triangle, with two edges being straight and the third being curved in an arch that follows the silhouette of a normal, at rest, human shoulder.

The two straight edges of each triangular side panel are approximately 11 inches to 13 inches in length and the curved edge of each triangular side panel is approximately 14 inches to 16 inches in length or the same as the length of the rectangular center panel.

Both shape and size specifications are duplicated for each layer of the heating device, which includes a top and bottom covering material and a heating element configuration that is contained within a sealed, water-tight vinyl envelope that is produced as one piece, with the three panels briefly connected at a point where the heating element wiring crosses from one panel to the other. (Refer to "DRAWING 1 of 1", FIG. 2.)

The outer edges of the top and bottom covering material of the three panels are then bound together, enclosing the sealed vinyl envelope.

The curved edge of each of the two triangular side panels is then bound to each of the two matching edges of the rectangular center panel.

This creates a 'one-size-fits-all', scoop-like pocket shape that fits as comfortably and securely on a small woman's shoulder, elbow or knee as it does on the same joints of a large man.

An approximate one-inch to two inch wide, adjustable strap, which is attachable at both ends via a fabric holding device, is an important component of the new electric heating device.

DETAILED DESCRIPTION OF THE DRAWINGS

Figure 1:
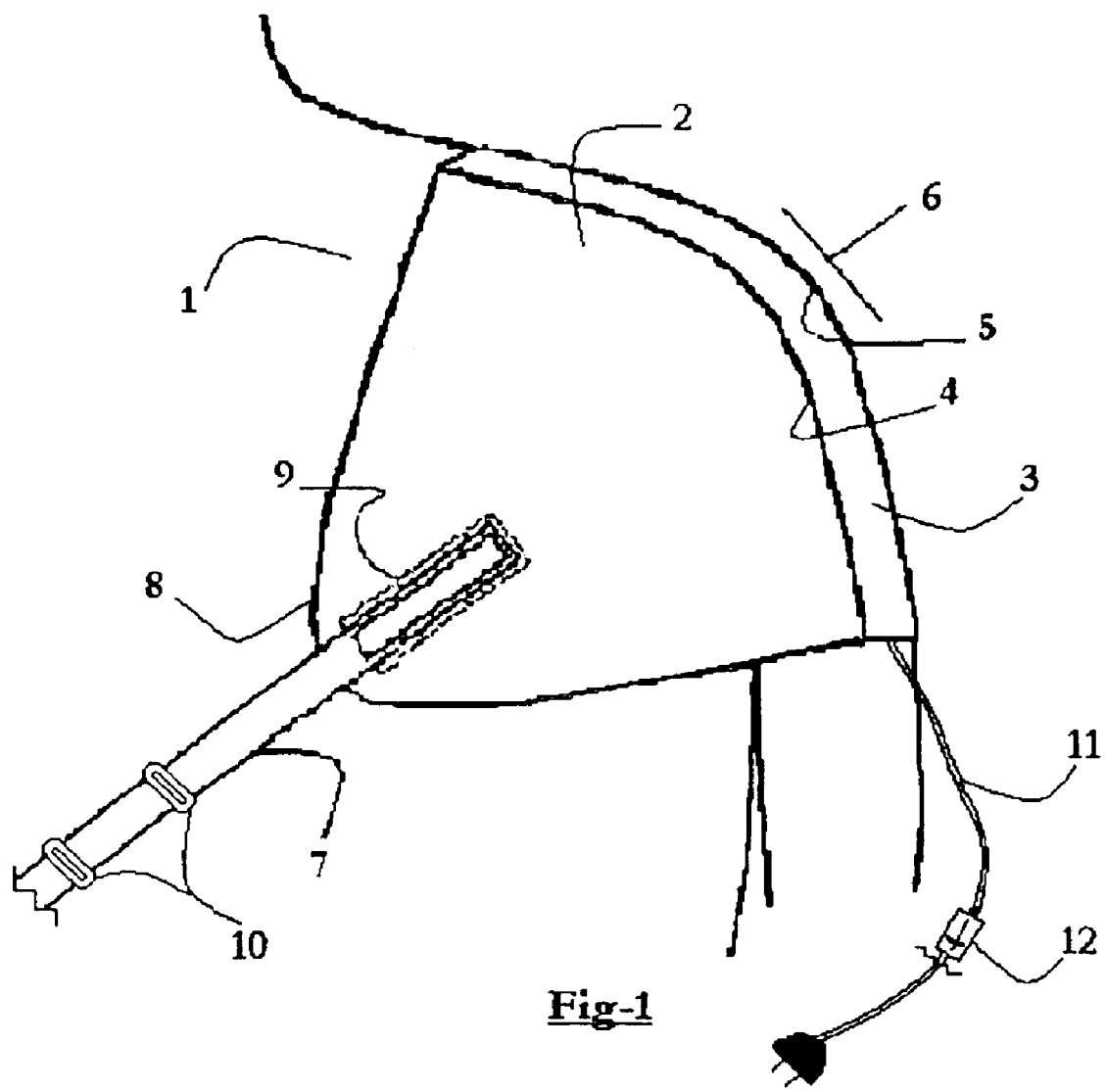
FIG. 1 is a perspective view showing the instant device in operative association with a user's shoulder.

Referring to FIG. 1, the present invention is shown snugly attached to a left or right human shoulder and torso 1 with two of the three panels that comprise the instant device in visible sight: one of the two triangular side panels 2 and the rectangular center panel 3.

At FIG. 1, the attachment of the curved edge of the visible triangular side panel 4, and the curved edge of the 'out-of view', triangular side panel 5 to each of the longer edges of the center rectangular panel 3 creates the desired three-dimensional scoop-like cup 6 that accommodates the curvatures of the shoulder, elbow and knee.

At FIG. 1, a cutaway section of one end of the adjustable strap 7 is shown attached to the distal end of the visible triangular side panel 8 via fastening closures 9 that comprise any type of appropriate fastener known in the art, for example, a hook or loop material such as Velcro, shown used in this depiction. Adjustability of strap is attained by way of two open 'slip buckles' 10 or other appropriate strap adjustment devices.

At FIG. 1, an electrical connection from heating device to a power source 11, and manual control in said electrical connection 12 including on-off positions and two or more heat settings.

Figure 2:
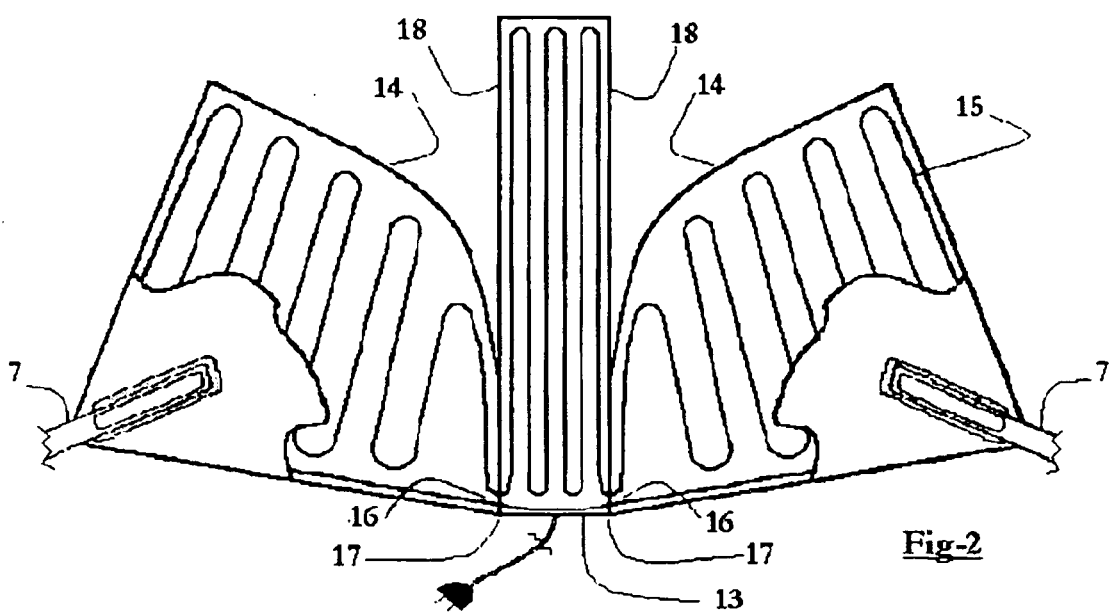
FIG. 2 is a perspective view of the instant device, showing a cutaway revealing the approximate layout of the heating elements therein.

Referring to FIG. 2, a cutaway of the sealed, vinyl envelope, heating element, constructed as one unit and attached at the base 13 of the central rectangular panel by both triangular side panels at their curved edges 14. Heating wires 15 that transverse throughout each of the three panels in general parallel lines, interconnect 16 at only the base end of the attachment of three panels 17, allowing full 'drapability' of the completed device.

At FIG. 2, the curved edge 14 of each triangular panel is attached along each of the 'lenght' edges 18 of the central rectangular panel, creating a curved, scoop-like, three-dimensional structure.

Figure 3:
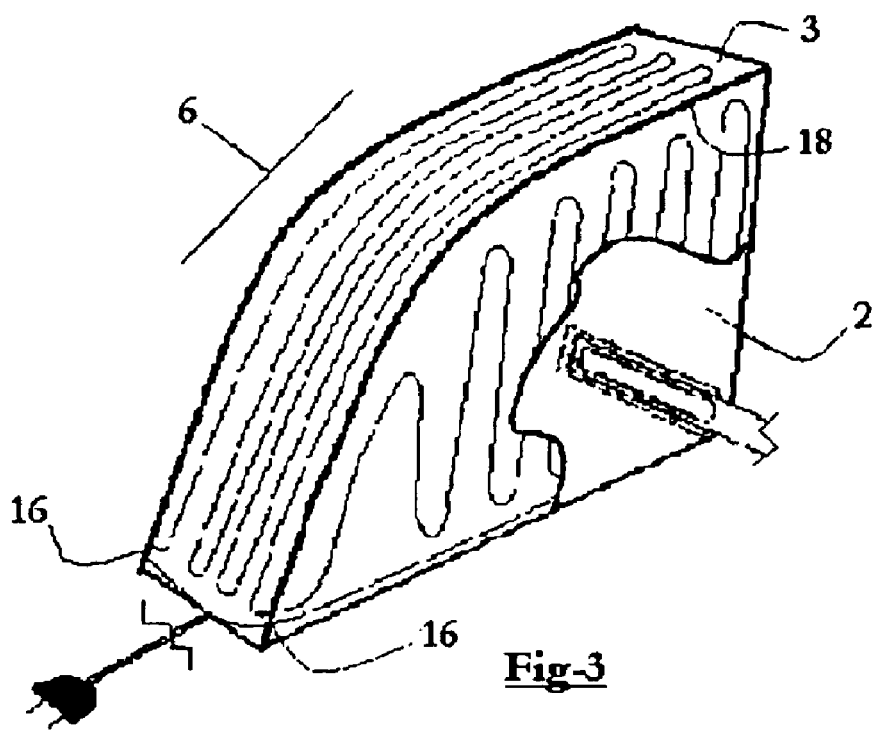
FIG. 3 is a perspective view of one side of the instant device, showing one of the triangular side panels attached to one edge of the rectangular center panel, with a cutaway of the heating elements and demonstrating how the single-point connection, located at one end of the attachment of the panels, allows for complete drapability.
Figure 4:
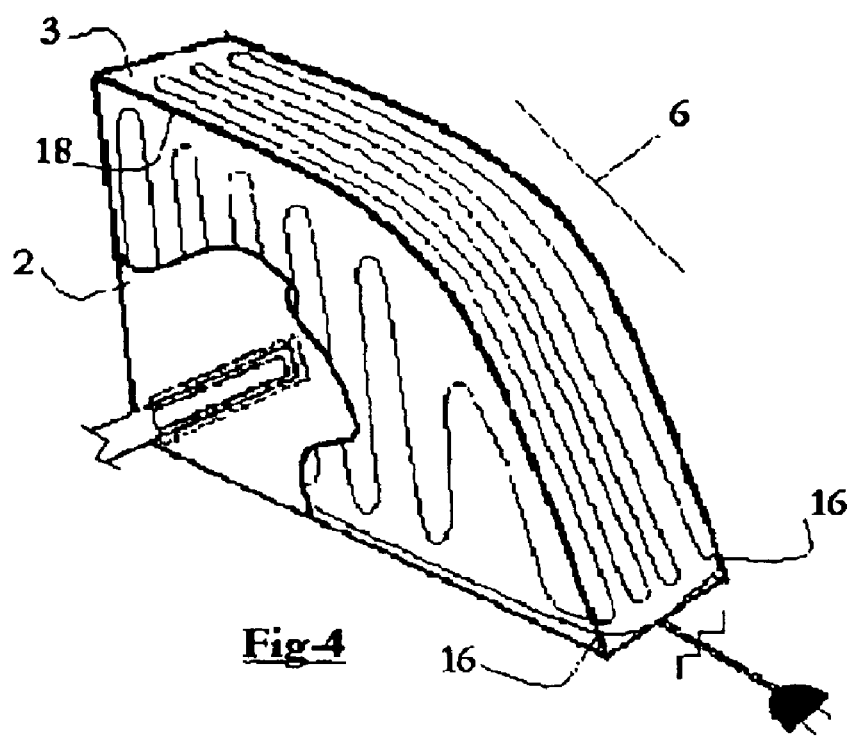
FIG. 4 is a perspective view of the opposite side of the instant device, which shows the second triangular side panel attached to the opposing edge of the rectangular center panel, showing a cutaway of the heating elements and demonstrating how the single-point connection, located at one end of the attachment of the panels, allows for complete drapability.

Referring to FIGS. 3 and 4, opposing views of each side of the new art, showing each of the triangular side panels 2 attached to opposing edges 18 of the rectangular center panel 3, with a cutaway of the heating elements and demonstrating how the wiring connections 16 between the three panels, located at one end of the attachment of the panels, allows for complete drapability 6.

What I claim as my invention is:

1. An electric heating device comprising:

a. a center rectangular panel with a width of approximately 3½ inches to 4½ inches and a length of approximately 14 inches to 16 inches, formed of front and back panels of a suitable fabric material, with a heating element sandwiched therein;

b. two triangular side panels, formed of front and back panels of the same fabric material as the rectangular panel, each with two straight-cut edges of equal lengths of approximately 11 inches to 13 inches and one curved edge that is cut in an arch of a normal curvature of a normal, at rest, adult having the same length as the length of the rectangular center panel, with heating elements sandwiched within each triangular side panel, with the curved edges of the triangular side panels attached to each of the 14 inches to 16 inch edges of the rectangular panel, to create a curved, scoop-like, three dimensional structure;

c. said heating elements that transverse throughout each of said rectangular and triangular side panels in general parallel lines, interconnected at only one end of a attachment of said rectangular and triangular side panels, allowing full 'drapability' of the completed device;

d. an electrical connection from said heating elements to a power source, and a manual control in said electrical connection including on-off positions and two or more heat settings.

2. The heating device of claim 1 wherein heating elements of said rectangular and triangular side panels are enclosed within one singular form-fitting waterproof vinyl cover, allowing for the use of a moistened cloth, which when placed between the device and the user's skin, causes a desired moist heat effect.

3. The heating device of claim 1 includes an adjustable holding belt, attached at each end to the distal corners of said triangular side panels, variable sizes are accomplished via an adjustable 'non-slip buckle', thereby accommodating a small woman or a large man.

* * * * *